(12) United States Patent
Goto et al.

(10) Patent No.: US 10,945,697 B2
(45) Date of Patent: Mar. 16, 2021

(54) X-RAY CT APPARATUS

(71) Applicant: Canon Medical Systems Corporation, Otawara (JP)

(72) Inventors: Takahiro Goto, Utsunomiya (JP); Shinsuke Tsukagoshi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 124 days.

(21) Appl. No.: 16/177,755

(22) Filed: Nov. 1, 2018

(65) Prior Publication Data

US 2019/0069868 A1 Mar. 7, 2019

Related U.S. Application Data

(63) Continuation of application No. PCT/JP2017/021020, filed on Jun. 6, 2017.

(30) Foreign Application Priority Data

Jun. 6, 2016 (JP) .............................. JP2016-112664

(51) Int. Cl.
*A61B 6/00* (2006.01)
*A61B 6/02* (2006.01)
(Continued)

(52) U.S. Cl.
CPC .............. *A61B 6/544* (2013.01); *A61B 6/027* (2013.01); *A61B 6/032* (2013.01); *A61B 6/0407* (2013.01);
(Continued)

(58) Field of Classification Search
CPC ....... A61B 6/027; A61B 6/032; A61B 6/0407; A61B 6/544; A61B 6/03; A61B 6/0457;
(Continued)

(56) References Cited

U.S. PATENT DOCUMENTS

| | | | | |
|---|---|---|---|---|
| 2004/0086076 | A1* | 5/2004 | Nagaoka | ................ A61B 6/463 378/4 |
| 2007/0116171 | A1* | 5/2007 | Hsieh | ................... A61B 6/4085 378/8 |

(Continued)

FOREIGN PATENT DOCUMENTS

| | | |
|---|---|---|
| JP | 2000-166912 | 6/2000 |
| JP | 2002-263097 | 9/2002 |

(Continued)

OTHER PUBLICATIONS

International Search Report dated Aug. 29, 2017 in PCT/JP2017/021020 filed Jun. 6, 2017 (with English Translation).
(Continued)

*Primary Examiner* — Chih-Cheng Kao
(74) *Attorney, Agent, or Firm* — Oblon, McClelland, Maier & Neustadt, L.L.P.

(57) ABSTRACT

An X-ray computed tomography (CT) apparatus according to an embodiment includes processing circuitry. The processing circuitry is configured to generate image data based on a detection result obtained by detecting X-rays transmitted through a subject with a detector. The processing circuitry is configured to specify a boundary between a first region and a second region in the image data, based on anatomical landmarks in the image data, and adjust setting of scan conditions relating to a tube current value in accordance with information relating to a position of the boundary.

11 Claims, 11 Drawing Sheets

(51) Int. Cl.
    *A61B 6/03* (2006.01)
    *A61B 6/04* (2006.01)
    *G06T 7/11* (2017.01)
    *G06T 7/13* (2017.01)

(52) U.S. Cl.
    CPC ............ *A61B 6/481* (2013.01); *A61B 6/5211* (2013.01); *A61B 6/545* (2013.01); *G06T 7/11* (2017.01); *G06T 7/13* (2017.01); *A61B 6/0487* (2020.08); *A61B 6/463* (2013.01); *G06T 2207/10081* (2013.01); *G06T 2207/20128* (2013.01); *G06T 2207/30004* (2013.01)

(58) Field of Classification Search
    CPC ....... A61B 6/463; A61B 6/481; A61B 6/5211; A61B 6/545
    See application file for complete search history.

(56) References Cited

U.S. PATENT DOCUMENTS

| | | | |
|---|---|---|---|
| 2008/0159611 A1* | 7/2008 | Tao | A61B 6/08 382/131 |
| 2009/0252286 A1 | 10/2009 | Mukumoto et al. | |
| 2012/0148131 A1 | 6/2012 | Couch et al. | |
| 2012/0148132 A1 | 6/2012 | Couch et al. | |
| 2012/0150505 A1 | 6/2012 | Couch et al. | |
| 2013/0177129 A1 | 7/2013 | Suzuki | |
| 2015/0092910 A1* | 4/2015 | Xing | A61B 6/542 378/8 |
| 2015/0139519 A1 | 5/2015 | Couch et al. | |
| 2015/0170363 A1 | 6/2015 | Couch et al. | |
| 2017/0123074 A1 | 5/2017 | Couch et al. | |
| 2017/0228860 A1 | 8/2017 | Couch et al. | |
| 2017/0243350 A1 | 8/2017 | Couch et al. | |

FOREIGN PATENT DOCUMENTS

| | | |
|---|---|---|
| JP | 2005-143948 | 6/2005 |
| JP | 2007-144172 | 6/2007 |
| JP | 2009-028559 | 2/2009 |
| JP | 2009-261915 | 11/2009 |
| JP | 2013-094253 | 5/2013 |
| JP | 2013-116143 | 6/2013 |
| JP | 2013-544605 | 12/2013 |
| JP | 2015-205065 | 11/2015 |

OTHER PUBLICATIONS

Written Opinion dated Aug. 29, 2017 in PCT/JP2017/021020 filed Jun. 6, 2017.

* cited by examiner

FIG.3
HELICAL SCAN 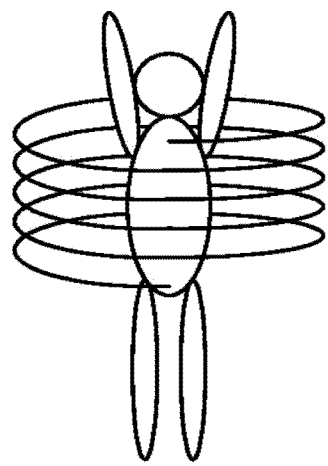 or NON-HELICAL SCAN 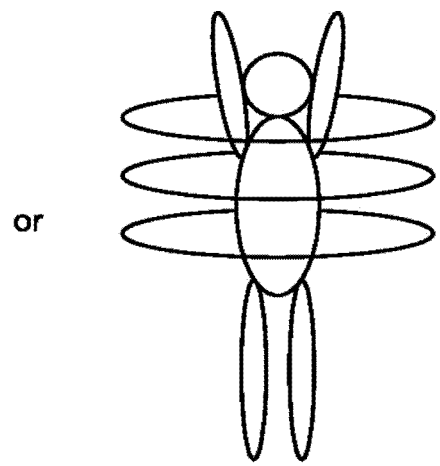
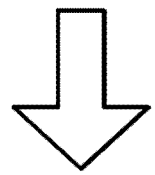
VOLUME DATA
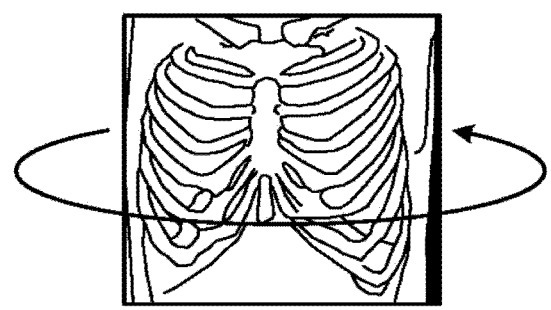
GENERATE POSITIONING IMAGE
FROM DESIRED DIRECTION

FIG.5

| IDENTIFI-CATION CODE | COORDINATES | | |
|---|---|---|---|
| | POSITIONING | SCAN | |
| | | NON-CONTRAST PHASE | CONTRAST PHASE |
| C1 | (x1, y1, z1) | (x'1, y'1, z'1) | (x'1, y'1, z'1) |
| C2 | (x2, y2, z2) | (x'2, y'2, z'2) | (x'2, y'2, z'2) |
| C3 | (x3, y3, z3) | (x'3, y'3, z'3) | (x'3, y'3, z'3) |
| C4 | (x4, y4, z4) | (x'4, y'4, z'4) | (x'4, y'4, z'4) |
| C5 | (x5, y5, z5) | (x'5, y'5, z'5) | (x'5, y'5, z'5) |
| C6 | (x6, y6, z6) | (x'6, y'6, z'6) | (x'6, y'6, z'6) |
| C7 | (x7, y7, z7) | (x'7, y'7, z'7) | (x'7, y'7, z'7) |
| C8 | (x8, y8, z8) | (x'8, y'8, z'8) | (x'8, y'8, z'8) |
| C9 | (x9, y9, z9) | (x'9, y'9, z'9) | (x'9, y'9, z'9) |
| C10 | (x10, y10, z10) | (x'10, y'10, z'10) | (x'10, y'10, z'10) |
| ⋮ | ⋮ | ⋮ | ⋮ |
| C31 | | | (x'31, y'31, z'31) |
| C32 | | | (x'32, y'32, z'32) |
| C33 | | | (x'33, y'33, z'33) |
| C34 | | | (x'34, y'34, z'34) |
| ⋮ | ⋮ | ⋮ | ⋮ | though PCT International Application No. PCT/JP2017/021020 filed on Jun. 6, 2017 which claims the benefit of priority from Japanese Patent Application No. 2016-112664 filed on Jun. 6, 2016, the entire contents of which are incorporated herein by reference.

X-RAY CT APPARATUS

CROSS-REFERENCE TO RELATED APPLICATIONS

This application is a continuation of PCT International Application No. PCT/JP2017/021020 filed on Jun. 6, 2017 which claims the benefit of priority from Japanese Patent Application No. 2016-112664 filed on Jun. 6, 2016, the entire contents of which are incorporated herein by reference.

FIELD

Embodiments described herein relate generally to an X-ray CT apparatus.

BACKGROUND

In prior art, auto exposure control (AEC) can be executed, in imaging using an X-ray computed tomography (CT) apparatus. In AEC, a tube current is automatically recommended in accordance with the body thickness of the subject. For example, in calculation of mA by AEC, the calculation is executed for the subject in the scan range. The scan range is set to any range on a positioning image (scanogram) by the operator, after the scanogram is acquired. Specifically, AEC is executed for the scan range set on the scanogram.

BRIEF DESCRIPTION OF THE DRAWINGS

FIG. 3 is a diagram for explaining three-dimensional scanogram imaging with a scan controller according to the first embodiment;

FIG. 5 is a diagram for explaining an example of processing of detecting a region with the detecting function according to the first embodiment;

DETAILED DESCRIPTION

According to an embodiment, an X-ray computed tomography (CT) apparatus includes processing circuitry. The processing circuitry is configured to generate image data based on a detection result obtained by detecting X-rays transmitted through a subject with a detector. The processing circuitry is configured to specify a boundary between a first region and a second region in the image data, based on anatomical landmarks in the image data, and adjust setting of scan conditions relating to a tube current value in accordance with information relating to a position of the boundary.

An embodiment of an X-ray computed tomography (CT) apparatus will be explained in detail hereinafter with reference to attached drawings. The following explanation illustrates a medical information processing system including the X-ray CT apparatus, as an example. In a medical information processing system 100 illustrated in FIG. 1, only one server apparatus and one terminal apparatus are illustrated, but actually the system may include a plurality of server apparatuses and terminal apparatuses. In addition, the medical information processing system 100 may include a medical image diagnostic apparatus, such as an X-ray diagnostic apparatus, a magnetic resonance imaging (MRI) apparatus, and an ultrasonic diagnostic apparatus.

First Embodiment

Figure 1:
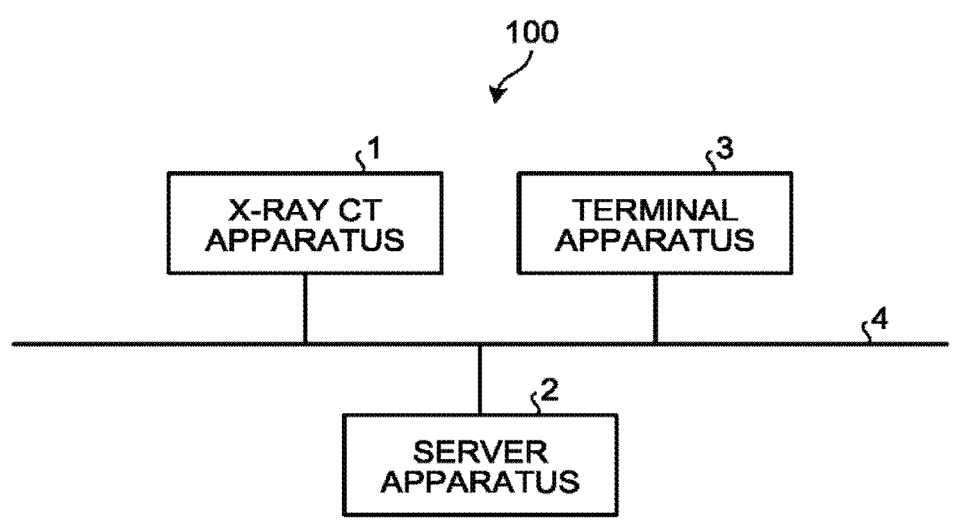
FIG. 1 is a diagram illustrating an example of configuration of a medical information processing system according to a first embodiment.

FIG. 1 is a diagram illustrating an example of configuration of the medical information processing system 100 according to the first embodiment. As illustrated in FIG. 1, the medical information processing system 100 according to the first embodiment includes an X-ray CT apparatus 1, a server apparatus 2, and a terminal apparatus 3. The X-ray CT apparatus 1, the server apparatus 2, and the terminal apparatus 3 are capable of mutually communicating directly or indirectly through an in-hospital local area network (LAN) 4 installed in the hospital, for example. For example, when a picture archiving and communication system (PACS) is introduced into the medical information processing system 100, the apparatuses mutually transmit and receive medical images and the like, in accordance with the digital imaging and communications in medicine (DICOM) standard.

In addition, for example, a hospital information system (HIS) and a radiology information system (RIS) are introduced into the medical information processing system 100, to manage various types of information. For example, the terminal apparatus 3 transmits an inspection order prepared in accordance with the system described above to the X-ray CT apparatus 1 and/or the server apparatus 2. The X-ray CT apparatus 1 acquires subject information from an inspection order directly received from the terminal apparatus 3, or a subject list (modality work list) for each modality prepared with the server apparatus 2 that has received the inspection order, to acquire X-ray CT image data for each subject. The X-ray CT apparatus 1 transmits the acquired X-ray CT image data and image data generated by performing various types of image processing on the X-ray CT image data, to the server apparatus 2. The server apparatus 2 stores the X-ray CT image data and the image data received from the X-ray CT apparatus 1, and generates image data from the X-ray CT image data, to transmit image data corresponding to an acquisition request from the terminal apparatus 3 to the terminal apparatus 3. The terminal apparatus 3 displays the image data received from the server apparatus 2, on a monitor or the like. The following is explanation of each of the apparatuses.

The terminal apparatus 3 is disposed in each clinical department in the hospital, and operated by a doctor working at each clinical department. The terminal apparatus 3 is, for example, a personal computer (PC), a tablet PC, a personal digital assistant (PDA), or a mobile phone. For example, the terminal apparatus 3 receives medical record information, such as subject's symptoms and doctor's observations, input by the doctor. The terminal apparatus 3 also receives an inspection order to order inspection with the X-ray CT apparatus 1, and transmits the input inspection order to X-ray CT apparatus 1 and/or the server apparatus 2. Specifically, the doctor of the clinical department operates the terminal apparatus 3, to read the reception information on the subject who has visited the hospital and information on the electronic medical record, perform medical examination on the corresponding subject, and input medical record information to the read electronic medical record. Thereafter, the doctor of the clinical department operates the terminal apparatus 3 to transmit an inspection order, in accordance with necessity of inspection with the X-ray CT apparatus 1.

The server apparatus 2 stores medical images (such as X-ray CT image data and image data acquired with the X-ray CT apparatus 1) acquired with a medical image diagnostic apparatus, and performs various types of image processing on the medical images. For example, the server apparatus 2 is a PACS server. For example, the server apparatus 2 receives a plurality of inspection orders from a plurality of terminal apparatuses 3 arranged in respective clinical departments, prepares a subject list for each of medical image diagnostic apparatuses, and transmits the prepared subject lists to the respective medical image diagnostic apparatuses. As an example, the server apparatus 2 receives inspection orders to execute inspection with the X-ray CT apparatus 1 from the terminal apparatuses 3 of the respective clinical departments, prepares a subject list, and transmits the prepared subject list to the X-ray CT apparatus 1. Thereafter, the server apparatus 2 stores the X-ray CT image data and the image data acquired with the X-ray CT apparatus 1, and transmits the X-ray CT image data and the image data to the terminal apparatus 3, in response to an acquisition request from the terminal apparatus 3.

Figure 2:
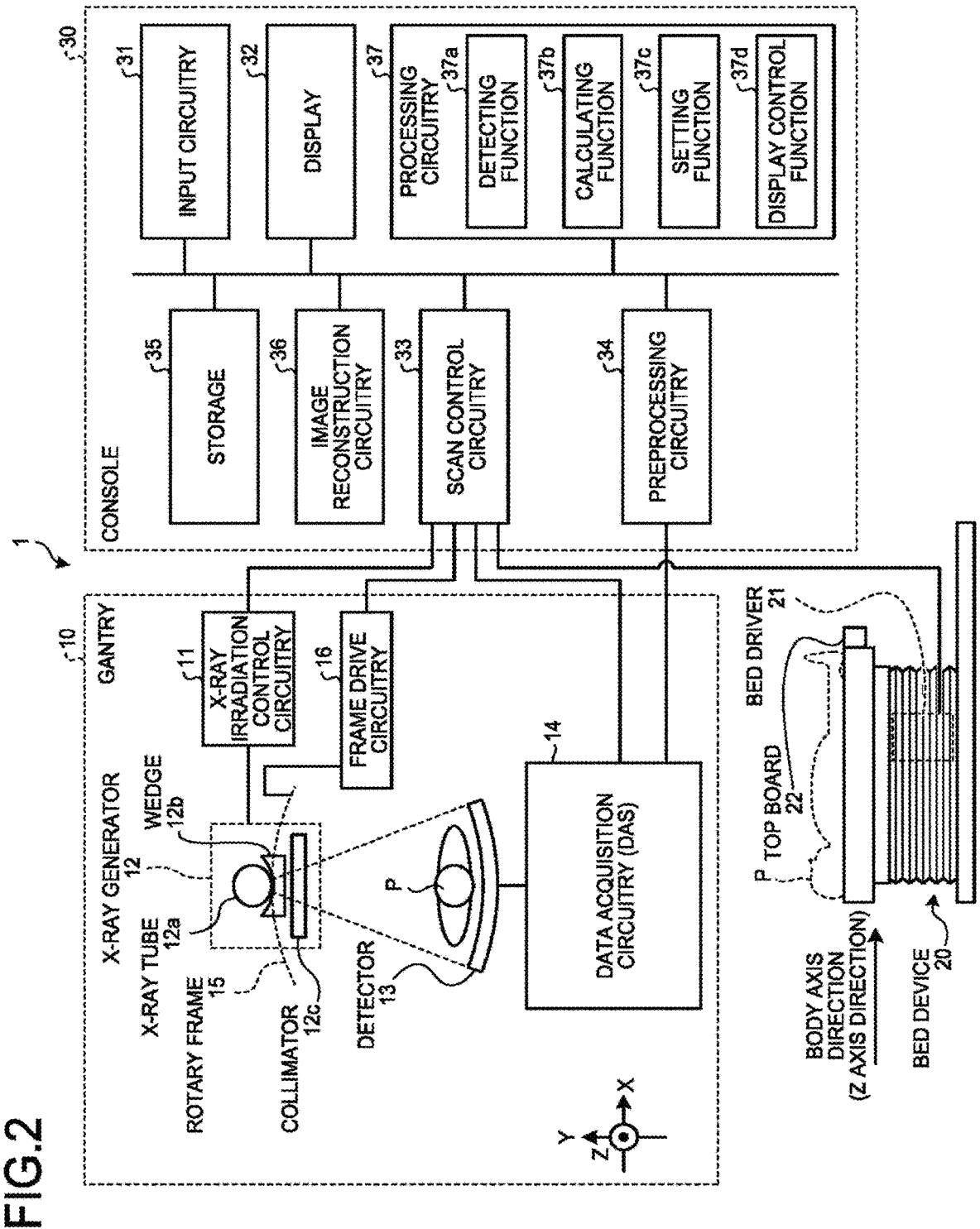
FIG. 2 is a diagram illustrating an example of configuration of an X-ray CT apparatus according to the first embodiment.

The X-ray CT apparatus 1 acquires X-ray CT image data for each subject, and transmits the acquired X-ray CT image data and image data generated by performing various types of image processing on the X-ray CT image data, to the server apparatus 2. FIG. 2 is a diagram illustrating an example of configuration of the X-ray CT apparatus 1 according to the first embodiment. As illustrated in FIG. 2, the X-ray CT apparatus 1 according to the first embodiment includes a gantry 10, a bed device 20, and a console 30.

The gantry 10 applies X-rays to the subject P (patient), to detect the X-rays transmitted through the subject P, and output the X-rays to the console 30. The gantry 10 includes X-ray irradiation control circuitry 11, an X-ray generator 12, a detector 13, data acquisition circuitry (data acquisition system: DAS) 14, a rotary frame 15, and frame drive circuitry 16.

The rotary frame 15 is a circular frame supporting the X-ray generator 12 and the detector 13 such that the X-ray generator 12 and the detector 13 are opposed with the subject P interposed therebetween, and rotated by the frame drive circuitry 16 described later at high speed with a circular orbital path with the subject P serving as the center.

The X-ray irradiation control circuitry 11 is a device supplying high voltage to an X-ray tube 12a, as a high-voltage generator. The X-ray tube 12a generates X-rays using the high-voltage supplied from the X-ray irradiation control circuitry 11. The X-ray irradiation control circuitry 11 adjusts the tube voltage and/or the tube current supplied to the X-ray tube 12a, under the control of scan control circuitry 33 described later, to adjust the X-ray quantity applied to the subject P.

The X-ray irradiation control circuitry 11 also switches a wedge 12b. The X-ray irradiation control circuitry 11 also adjusts the aperture of a collimator 12c, to adjust the irradiation range (such as a fan angle and a cone angle). The present embodiment may include the case where the operator manually switches a plurality of types of wedges.

The X-ray generator 12 generates X-rays, to apply the generated X-rays to the subject P. The X-ray generator 12 includes the X-ray tube 12a, the wedge 12b, and the collimator 12c.

The X-ray tube 12a is a vacuum tube applying an X-ray beam to the subject P using high voltage supplied from the high-voltage generator that is not illustrated. The X-ray tube 12a applies an X-ray beam to the subject P, with rotation of the rotary frame 15. The X-ray tube 12a generates an X-ray beam spreading with a fan angle and a cone angle. For example, under the control of the X-ray irradiation control circuitry 11, the X-ray tube 12a is capable of continuously exposing the whole circumference of the subject P to X-rays for full reconstruction, and continuously exposing an exposure range (180°+ fan angle) enabling half reconstruction to X-rays for half reconstruction. In addition, under the control of the X-ray irradiation control circuitry 11, the X-ray tube 12a is capable of intermittently radiating X-rays (pulse X-rays) at a preset position (tube bulb position). The X-ray irradiation control circuitry 11 is also capable of modulating intensity of X-rays radiated from the X-ray tube 12a. For example, the X-ray irradiation control circuitry 11 increases the intensity of X-rays radiated from the X-ray tube 12a at a specific tube bulb position, and decreases the intensity of X-rays radiated from the X-ray tube 12a, in a range other than the specific tube bulb position.

The wedge 12b is an X-ray filter to adjust the X-ray quantity of X-rays radiated from the X-ray tube 12a. Specifically, the wedge 12b is a filter transmitting and attenuating X-rays radiated from the X-ray tube 12a such that the X-rays applied from the X-ray tube 12a to the subject P has a predetermined distribution. For example, the wedge 12b is a filter obtained by processing aluminum to have a predetermined target angle and a predetermined thickness. The wedge is also referred to as a wedge filter or a bow-tie filter.

The collimator 12c is a slit to narrow down the irradiation range of X-rays with the X-ray quantity adjusted with the wedge 12b, under the control of the X-ray irradiation control circuitry 11 described later.

The frame drive circuitry 16 drives and rotates the rotary frame 15, to turn the X-ray generator 12 and the detector 13 on the circular orbital path with the subject P serving as the center.

The detector 13 is a two-dimensional array type detector (area detector) detecting X-rays transmitted through the subject P, and has a structure in which a plurality of lines of detecting elements are arranged along the body axis direction (Z axis direction in FIG. of the subject P, and X-ray detecting elements for a plurality of channels are arranged in each line of the detecting elements. Specifically, the detector 13 in the first embodiment includes X-ray detecting elements arranged in a plurality of lines, such as 320 lines, along the body axis direction of the subject P, and is capable of detecting X-rays transmitted through the subject P in a wide range, such as a range including the lungs and the heart of the subject P.

The data acquisition circuitry 14 is a DAS, and acquires projection data from X-ray detection data detected with the detector 13. For example, the data acquisition circuitry 14 subjects the X-ray intensity distribution data detected with the detector 13 to amplification, A/D conversion, and/or sensitivity correction processing between channels, to generate projection data, and transmits the generated projection data to the console 30 described later. For example, when X-rays are continuously radiated from the X-ray tube 12*a* during rotation of the rotary frame 15, the data acquisition circuitry 14 acquires pieces of projection data for the whole circumference (for 360°). In addition, the data acquisition circuitry 14 correlates the tube bulb position with each piece of the acquired projection data, and transmits the data to the console 30 described later. The tube bulb position serves as information indicating the projection direction of the projection data. A preprocessing circuitry 34 described later may perform the sensitivity correction processing between channels.

The bed device 20 is a device on which the subject P is placed, and includes a bed driver 21, and a top board 22, as illustrated in FIG. 2. The bed driver 21 moves the top board 22 in the Z axis direction, to move the subject P into the rotary frame 15. The top board 22 is a board on which the subject P is placed.

The gantry 10 executes, for example, helical scan in which the rotary frame 15 is rotated while the top board 22 is moved, to scan the subject P in a helical manner. As another example, the gantry 10 executes conventional scan in which the rotary frame 15 is rotated, with the position of the subject P fixed after the top board 22 is moved, to scan the subject P with a circular orbital path. As another example, the gantry 10 executes a step-and-shoot method in which the position of the top board 22 is moved at regular intervals to perform conventional scan in a plurality of scan areas.

The console 30 receives operator's operations of the X-ray CT apparatus 1, and reconstructs X-ray CT image data using projection data acquired with the gantry 10. As illustrated in FIG. 2, the console 30 includes input circuitry 31, a display 32, scan control circuitry 33, the preprocessing circuitry 34, storage 35, image reconstruction circuitry 36, and processing circuitry 37.

The input circuitry 31 includes a mouse, a keyboard, a trackball, a switch, a button, and/or joystick used by the operator of the X-ray CT apparatus 1 to input various instructions and various settings, and transfers information instructions and settings received from the operator to the processing circuitry 37. For example, the input circuitry 31 receives imaging conditions of the X-ray CT image data, reconstruction conditions for reconstruction of the X-ray CT image data, and/or image processing conditions for the X-ray CT image data. The input circuitry 31 also receives an operation to select inspection for the subject. The input circuitry 31 also receives a designation operation to designate a region on the image.

The display 32 is a monitor referred to by the operator. The display 32 displays image data generated from the X-ray CT image data for the operator, and displays graphical user interface (GUI) to receive various instructions and various settings from the operator through the input circuitry 31, under the control of the processing circuitry 37. The display 32 also displays a planning picture of a scan plan, and a picture being scanned. The display 32 also displays a virtual subject image including dose information and image data. The virtual subject image displayed on the display 32 will be described in detail later.

The scan control circuitry 33 controls operations of the X-ray irradiation control circuitry 11, the frame drive circuitry 16, the data acquisition circuitry 14, and the bed driver 21, under the control of the processing circuitry 37, to control processing of acquiring projection data in the gantry 10. Specifically, the scan control circuitry 33 controls projection data acquisition processing in imaging to acquire positioning images (scanogram), and in main imaging (scan) to acquire images used for diagnosis. The X-ray CT apparatus 1 according to the first embodiment is capable of imaging two-dimensional scanograms and three-dimensional scanograms.

For example, the scan control circuitry 33 fixes the X-ray tube 12*a* to a position of 0° (position in the front direction with respect to the subject), and performs imaging continuously while moving the top board at fixed speed, to image two-dimensional scanograms. As another example, the scan control circuitry 33 fixes the X-ray tube 12*a* to a position of 0°, and repeats imaging intermittently in synchronization with movement of the top board, to image two-dimensional scanograms. The scan control circuitry 33 is capable of imaging positioning images in a desired direction (for example, a side surface direction), as well as the front direction with respect to the subject.

The scan control circuitry 33 acquires pieces of projection data for the whole circumference of the subject in imaging of scanograms, to image three-dimensional scanograms. FIG. 3 is a diagram for explaining three-dimensional scanogram imaging with the scan control circuitry 33 according to the first embodiment. For example, as illustrated in FIG. 3, the scan control circuitry 33 acquires projection data for the whole circumference of the subject by helical scan or non-helical scan. The scan control circuitry 33 performs helical scan or non-helical scan with a dose lower than that of main imaging, in a wide range such as the whole chest region, the whole abdominal region, the whole upper half of the body, or the whole body of the subject. For example, the step-and-shoot scan as described above is performed as non-helical scan.

As described above, by acquiring projection data for the whole circumference of the subject with the scan control circuitry 33, the image reconstruction circuitry 36 described later is enabled to reconstruct three-dimensional X-ray CT image data (volume data), and generate a positioning image from a desired direction using the reconstructed volume data, as illustrated in FIG. 3. The operator may set whether to image a positioning image in a two-dimensional manner or a three-dimensional manner, as desired. As another example, it may be set in advance in accordance with details of inspection.

With reference to FIG. 2 again, the preprocessing circuitry 34 subjects the projection data generated with the data acquisition circuitry 14 to logarithmic transformation and correction such as offset correction, sensitivity correction, and beam hardening correction, to generated corrected projection data. Specifically, the preprocessing circuitry 34 generates corrected projection data for each of projection data of the positioning image generated with the data acquisition circuitry 14 and projection data acquired by main imaging, and stores the data in the storage 35.

The storage 35 stores projection data generated with the preprocessing circuitry 34. Specifically, the storage 35 stores projection data of the positioning image generated with the preprocessing circuitry 34 and diagnostic projection data acquired by main imaging. The storage 35 also stores image data generated with the image reconstruction circuitry 36 described later, and a virtual subject image. The storage 35 also properly stores a processing result obtained with the processing circuitry 37 described later. The virtual subject image and the processing result obtained with the processing circuitry 37 will be described later.

The image reconstruction circuitry 36 recons X-ray CT image data using the projection data stored in the storage 35. Specifically, the image reconstruction circuitry 36 reconstructs X-ray CT image data from each of the projection data of the positioning image and projection data of the image used for diagnosis. Various methods can be used as the reconstruction method, such as back projection. Examples of back projection includes back projection by filtered back projection (FEP). As another example, the image reconstruction circuitry 36 may reconstruct X-ray CT image data using successive approximation.

The image reconstruction circuitry 36 performs various types of image processing on the X-ray CT image data, to generate image data. The image reconstruction circuitry 36 stores the reconstructed X-ray CT image data and image data generated by various types e processing in the storage 35.

The processing circuitry 37 controls operations of the gantry 10, the bed device 20, and the console 30, to control the whole X-ray CT apparatus 1. Specifically, the processing circuitry 37 controls the scan control circuitry 33, to control CT scan performed in the gantry 10. The processing circuitry 37 also controls the image reconstruction circuitry 36, to control image reconstruction processing and image generation processing in the console 30. The processing circuitry 37 also performs control to display various types of image data stored in the storage 35, on the display 32.

The processing circuitry 37 also performs a detecting function 37*a*, a calculating function 37*b*, a setting function 37*c*, and a display control function 37*d*, as illustrated in FIG. 2. For example, each of the processing functions executed with the detecting function 37*a*, the calculating function 37*b*, the setting function 37*c*, and the display control function 37*d* serving as the constituent elements illustrated in FIG. 2 is stored in the form of a program executable with the computer in the storage 35. The processing circuitry 37 is a processor reading each program from the storage 35, and executing the program, to achieve the function corresponding to the program. In other words, the processing circuitry 37 in a state of reading the programs has the functions illustrated in the processing circuitry 37 of FIG. 2. The data acquisition circuitry 14 explained in the present embodiment is an example of processing circuitry described in the claims. The image reconstruction circuitry 36 is an example of processing circuitry described in the claims. The processing circuitry 37 is an example of processing circuitry described in the claims. The setting function 37*c* corresponds to the setting unit and the mode setting unit described in the claims.

The term "processor" used in the explanation described above means, for example, a central processing unit (CPU), a graphics processing unit (CPU), or a circuit such as an application specific integrated circuit (ASIC) and a programmable logical device (such as a simple programmable logic device: SPLD, a complex programmable logic device: CPLD, and a field programmable gate array: FPGA)). The processor achieves the functions by reading and executing programs stored in the storage circuitry. Instead of storing programs in the storage circuitry, the processor may have a structure in which programs are directly incorporated into the circuit of the processor. In this case, the processor achieves the functions by reading and executing programs incorporated into the circuit. Each processor in the present embodiment is not limited to the case where each processor is configured as a single circuit, but a plurality of independent circuits may be combined as a processor, to achieve the functions.

The detecting function 37*a* detects each of a plurality of regions in the subject included in the three-dimensional image data. Specifically, the detecting function 37*a* detects regions such as organs included in the three-dimensional X-ray CT image data (volume data) reconstructed by the image reconstruction circuitry 36. For example, the detecting function 37*a* detects regions such as organs on the basis of anatomical landmarks, for at least one of volume data of the positioning image and volume data of the image used for diagnosis. The anatomical landmarks are points indicating features of regions such as a specific bone, an organ, a blood vessel, a nerve, and a lumen. Specifically, the detecting function 37*a* detects anatomical landmarks such as a specific organ and a bone, to detect the bone, the organ, the blood vessel, the nerve, and/or the lumen included in the volume data. The detecting function 37*a* is also capable of detecting the position of the head, the neck, the chest, the abdomen, and/or the leg included in the volume data, by detecting characteristic landmarks of the human body. The region explained in the present embodiment means the bone, the organs, the blood vessels, the nerves, and the lumen, including their positions. The following is explanation of an example of detection of the region with the detecting function 37*a*.

For example, the detecting function 37*a* extracts anatomical landmarks from the voxel values included in the volume data, in the volume data of the positioning image or the volume data of the image used for diagnosis. Thereafter, the detecting function 37*a* compares three-dimensional positions of the anatomical landmarks in information such as a textbook with the positions of landmarks extracted from the volume data, to remove incorrect landmarks from the landmarks extracted from the volume data, and optimize the positions of the landmarks extracted from the volume data. In this manner, the detecting function 37*a* detects each region of the subject included in the volume data. As an example, first, the detecting function 37*a* extracts anatomical landmarks included in the volume data using supervised machine learning. The supervised machine learning is constructed using a plurality of teacher images in which correct anatomical landmarks are manually arranged. For example, decision forest or the like is used.

Figure 4A:
FIG. 4A is a diagram for explaining an example of processing of detecting a region with a detecting function according to the first embodiment.
Figure 4B:
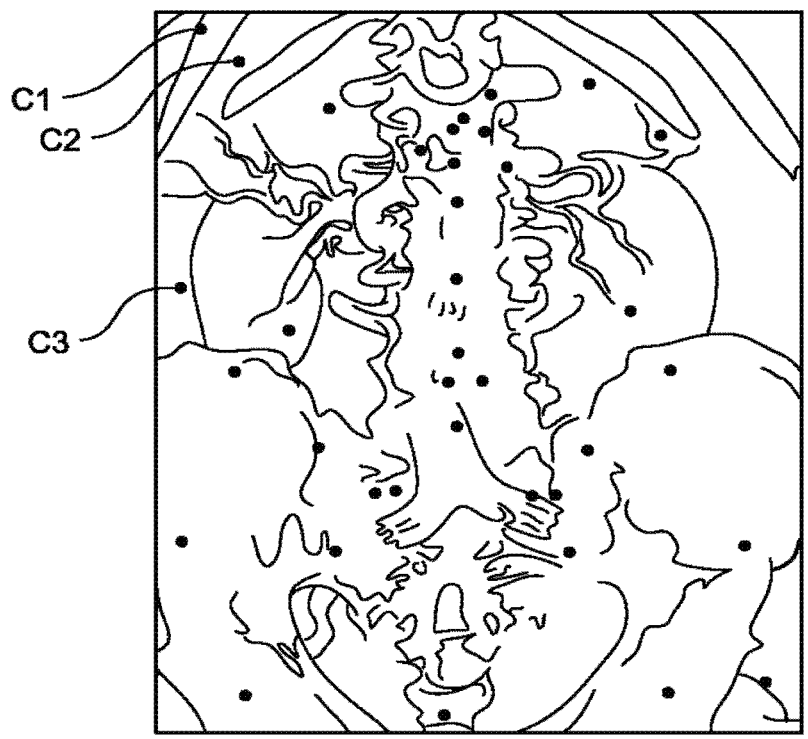
FIG. 4B is a diagram for explaining an example of processing of detecting a region with the detecting function according to the first embodiment.
Figure 6:
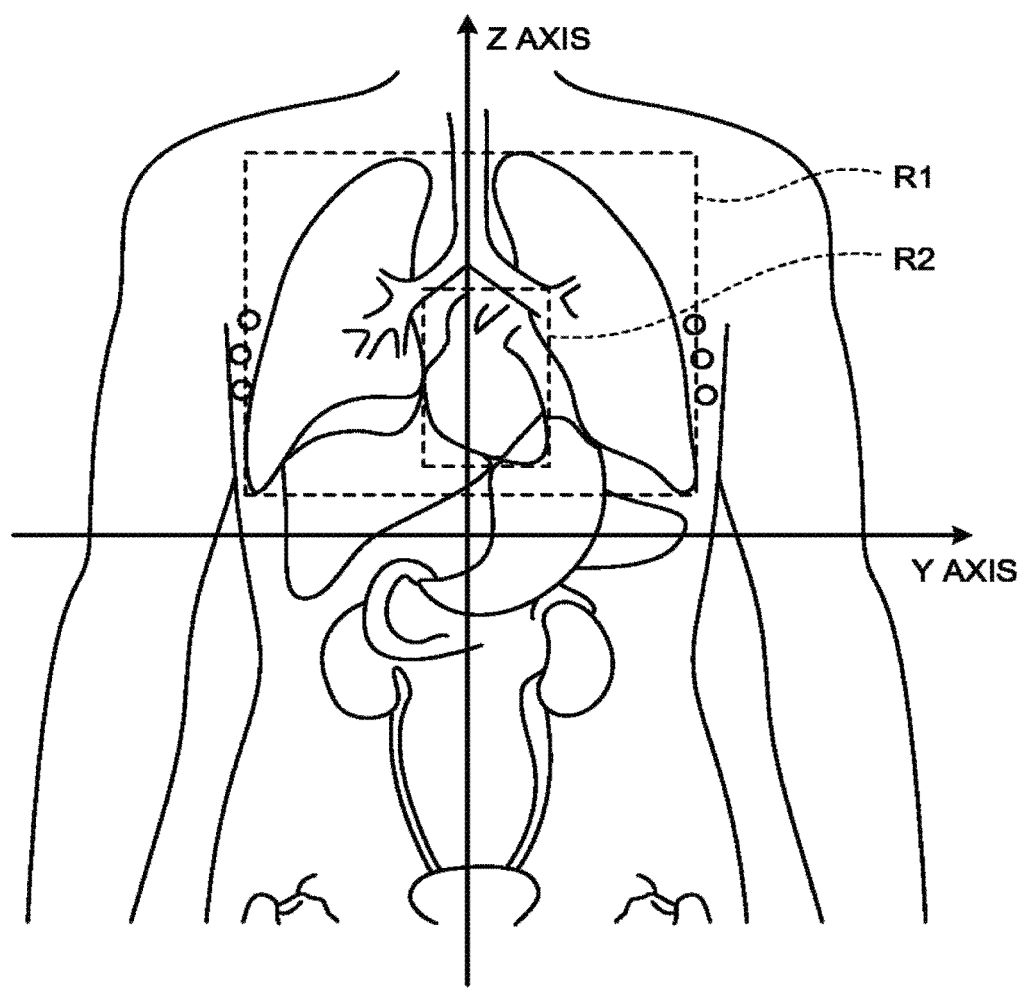
FIG. 6 is a diagram for explaining an example of processing of detecting a region with the detecting function according to the first embodiment.

In addition, the detecting function 37*a* compares a model indicating a three-dimensional positional relation of anatomical landmarks in the body with the extracted landmarks, to optimize the extracted landmarks. The model described above is constructed using the teacher images described above. For example, a point distribution model is used. Specifically, the detecting function 37*a* compares a model in which the shapes and positional relation of the regions, and points peculiar to the regions are defined on the basis of a plurality of teacher images in which correct anatomical landmarks are manually arranged, with the extracted landmarks, to remove incorrect landmarks, and optimize the landmarks. The following is explanation of an example of processing of detecting regions with the detecting function 37a, with reference to FIG. 4A, FIG. 4B, FIG. 5, and FIG. 6. FIG. FIG. 4B, FIG. 5, and FIG. 6 are diagrams for explaining an example of processing of detecting regions with the detecting function 37a according to the first embodiment. In FIG. 4A and FIG. 4B, landmarks are arranged in a two-dimensional manner, but actually landmarks are arranged in a three-dimensional manner. For example, the detecting function 37a applies a supervised machine learning algorithm to the volume data, to extract voxels (black points in the drawing) regarded as anatomical landmarks, as illustrated in FIG. 4A. Thereafter, the detecting function 37a fits the positions of the extracted voxels to a model defining the shapes and positional relation of the regions, and points peculiar to the regions, to remove incorrect landmarks in the extracted voxels, and extract only voxels corresponding to more correct landmarks, as illustrated in FIG. 4B.

The detecting function 37a provides the extracted landmarks (voxels) with identification codes to identify the landmarks indicating the features of the regions, and stores information correlating the identification codes with the positional (coordinate) information on respective landmarks and accompanying the image data, in the storage 35. For example, as illustrated in FIG. 4B, the detecting function 37a provides the extracted landmarks (voxeis) with identification codes, such as C1, C2, and C3. The detecting function 37a causes the identification codes accompanying the respective pieces of data subjected to detection processing, and stores them in the storage 35. Specifically, the detecting function 37a detects the region of the subject included in volume data reconstructed from at least one projection data, among the projection data of the positioning image, the projection data acquired in a non-contrast state, and projection data acquired in a contrast state with a contrast medium.

For example, as illustrated in FIG. 5, the detecting function 37a attaches information correlating the identification codes with coordinates of the respective voxels detected from the volume data ("positioning" in the drawing) of the positioning image to the volume data, and tores them in the storage 35. As an example, the detecting function 37a extracts coordinates of landmarks from the volume data of the positioning image, and correlates "identification code: C1, coordinates $(x_1, y_1, z_1)$". "identification code: C2, coordinates $(x_2, y_2, z_2)$" and the like with the volume data, to store them, as illustrated in FIG. 5. In this manner, the detecting function 37a is enabled to recognize what landmarks are arranged in what positions in the volume data of the positioning image, and detect each region, such as an organ, on the basis of these pieces of information.

In addition, for example, as illustrated in FIG. 5, the detecting function 37a attaches information correlating coordinates of respective voxels detected from the volume data ("scan" in the drawing) of the image for diagnosis with the identification codes to the volume data, and stores them in storage 35. In the scan, the detecting function 37a is capable of extracting coordinates of landmarks from each of the volume data ("contrast phase" in the drawing) in a contrast state with a contrast medium, and the volume data ("non-contrast phase" in the drawing) in a non-contrast state, and correlating the identification codes with the extracted coordinates.

As an example, the detecting function 37a extracts coordinates of landmarks from the volume data of the non-contrast phase, in the volume data of the image for diagnosis, and correlates "identification code: C1, coordinates $(x'_1, y'_1, z'_1)$", "identification code: G2, coordinates $(x'_2, y'_2, z'_2)$" and the like with the volume data, to store them, as illustrated in FIG. 5. The detecting function 37a also extracts coordinates of landmarks from the volume data of the contrast phase, in the volume data of the image for diagnosis, and correlates "identification code: C1, coordinates $(x'_1, y'_1, z'_1)$", "identification code: C2, coordinates $(x'_2, y'_2, z'_2)$" and the like with the volume data, to store them, as illustrated in FIG. 5. When landmarks are extracted from the volume data of the contrast phase, the landmarks include landmarks that become extractable by contrast radiography. For example, when landmarks are extracted from the volume data of the contrast phase, the detecting function 37a is capable of extracting blood vessels imaged with a contrast medium. Accordingly, in the case of the volume data of the contrast phase, as illustrated in FIG. 5, the detecting function 37a correlates identification codes C31, C32, C33, and C34, and the like to identify each of the blood vessels to coordinates $(x'_{31}, y'_{31}, z'_{31})$ to coordinates $(x'_{34}, y'_{34}, z'_{34})$ of landmarks such as blood vessels extracted by contrast radiography.

As described above, the detecting function 37a is capable of recognizing what landmarks exist in what positions in the volume data of the positioning image or the image for diagnosis, and detecting regions, such as organs, on the basis of these pieces of information. For example, the detecting function 37a detects the position of the target region using information on an anatomical positional relation between the target region serving as the target of detection and regions around the target region. As an example, when the target region is "lungs", the detecting function 37a acquires coordinate information correlated with the identification code indicating the features of the lungs, and acquires coordinate information correlated with identification codes indicating the regions around the "lungs", such as "ribs", "collarbones", "heart", and "diaphragm". Thereafter, the detecting function 37a extracts the area of the "lungs" in the volume data using information on an anatomical positional relation between the "lungs" and the surrounding regions, and the acquired coordinate information.

For example, as illustrated in FIG. 6, the detecting function 37a extracts an area R1 corresponding to the "lungs" in the volume data, from information on the positional relation such as "pulmonal apex: 2 to 3 cm above the collarbone" and "the lower end of the lung: as high as the seventh rib", and the coordinate information on each region. Specifically, the detecting function 37a extracts coordinate information on the voxel of the area R1 in the volume data. The detecting function 37a correlates the extracted coordinate information with the region information, attaches the information to the volume data, and stores them in the storage 35. In the same manner, as illustrated in FIG. 6, the detecting function 37a is capable of extracting an area R2 corresponding to the "heart" in the volume data.

In addition, the detecting function 37a detects a position included in the volume data, on the basis of the landmarks defining the positions of the head, the chest, and the like in the human body. The positions of the head, the chest, and the like in the human body can be defined as desired. For example, when the part from the seventh cervical vertebra to the lower end of the lungs is defined as the chest, the detecting function a detects a part from the landmark corresponding to the seventh cervical vertebra to the landmarks corresponding to the lower end of the lungs as the chest. The detecting function 37a is capable of detecting a region by various methods, as well as the method using anatomical landmarks described above. For example, the detecting function 37a is capable of detecting a region included in the volume data, by area expansion method based on voxel values.

The calculating function 37b calculates dose information on the region detected with the detecting function 37a. The setting function 37c adjusts the set range for which the tube current (mA) is set, in accordance with the boundary between the regions detected with the detecting function 37a. The display control function 37d performs control to display various types of display information on the display 32. For example, the display control function 37d performs control to display various types of image data stored in the storage 35 on the display 32. In addition, the display control function 37d performs control to display the setting adjusted with the setting function 37c on the display 32. The details of the calculating function 37b, the setting function 37c, and the display control function 37d will be described later.

The whole configuration of the X-ray CT apparatus 1 according to the first embodiment has been explained above. Under such configuration, the X-ray CT apparatus 1 according to the first embodiment enables modulation of the tube current suitable for the region to be imaged. As described above, in a conventional X-ray CT apparatus, AEC is executed for the scan range that is set as desired on the scanogram by the operator. In AEC, a tube current value is set at a predetermined position in the scan range, and the tube current is modulated to the set tube current value. As an example, in AEC, a tube current value is calculated on the basis of absorption of X rays (body thickness) for each rotation of the X-ray tube, and the tube current is modulated to the tube current value calculated during each rotation.

However, in the conventional X-ray CT apparatus described above, when the calculation unit (for example, one rotation of the X-ray tube) to calculate the tube current value includes a region with markedly different X-ray absorption, high tube current value is set to secure the image quality of the region with large X-ray absorption. Accordingly, when the calculation unit for which the tube current value is calculated includes a region with small X-ray absorption and a region with large X-ray absorption, the dose of the region with small X-ray absorption may increase. For this reason, the X-ray CT apparatus 1 according to the first embodiment enables modulation of the tube current suitable for the region to be imaged, under the control of the processing circuitry 37 described in detail hereinafter.

Specifically, in the X-ray CT apparatus 1 according to the first embodiment, the detector 13 detects X-rays transmitted through the subject, and the data acquisition circuitry 14 acquires projection data on the basis of the detection result. The image reconstruction circuitry 36 generates image data from the projection data. The detecting function 37a acquires positional information on a plurality of regions in the image data. The setting function 37c specifies the boundary between a first region and a second region in the image data on the basis of the positional information, and adjusts setting of the scan conditions relating to the tube current value in accordance with the boundary. More specifically, the detecting function 37a detects regions from the scanogram, and the setting function 37c sets a scan range including the region serving as the scan target. The setting function 37c sets the scan range such that the calculation unit of the tube current value is partitioned in the boundary between the first region and the second region.

Figure 7:
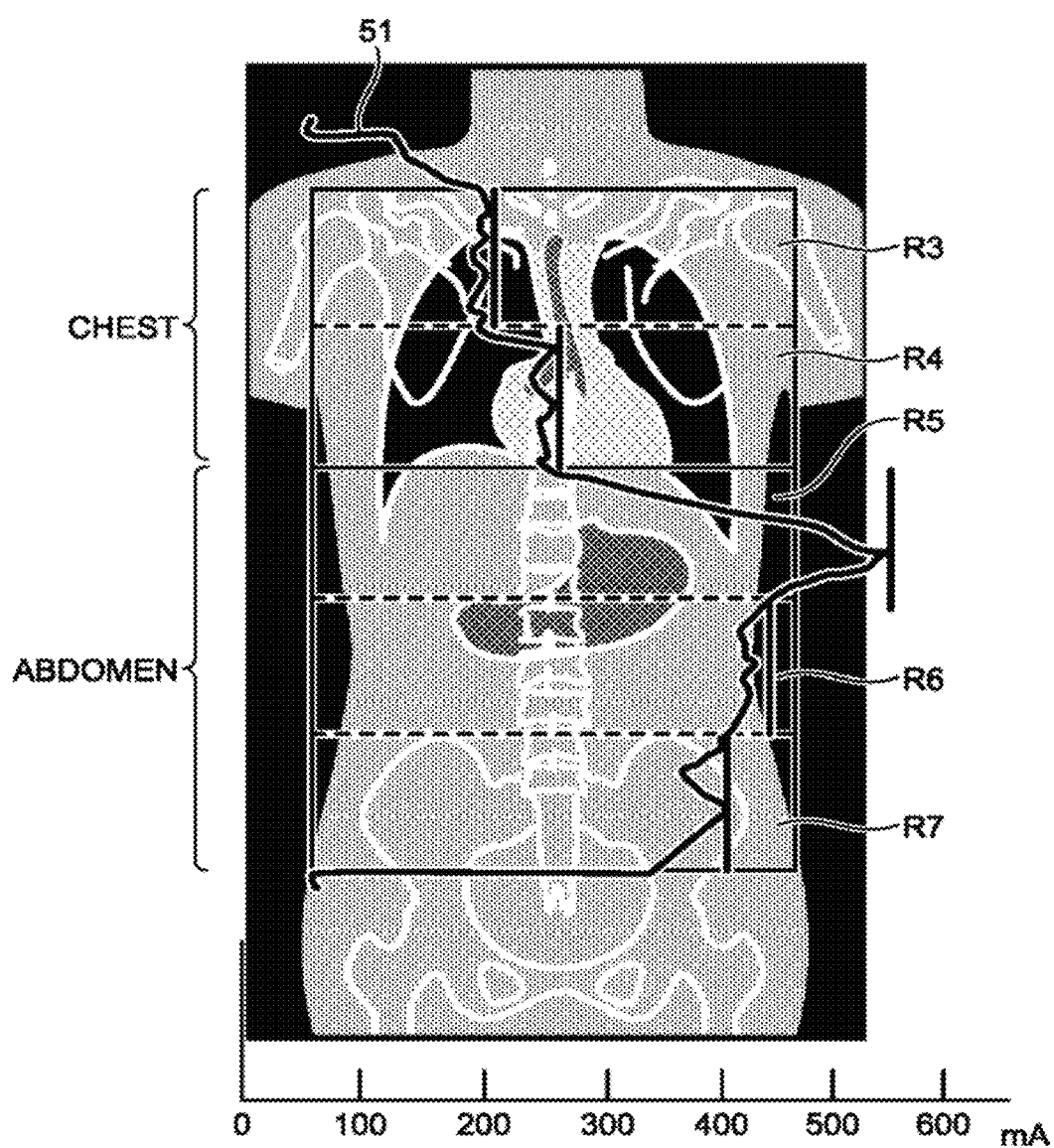
FIG. 7 is a diagram for explaining an example of the case of calculating a tube current for each rotation of an X-ray tube.
Figure 8:
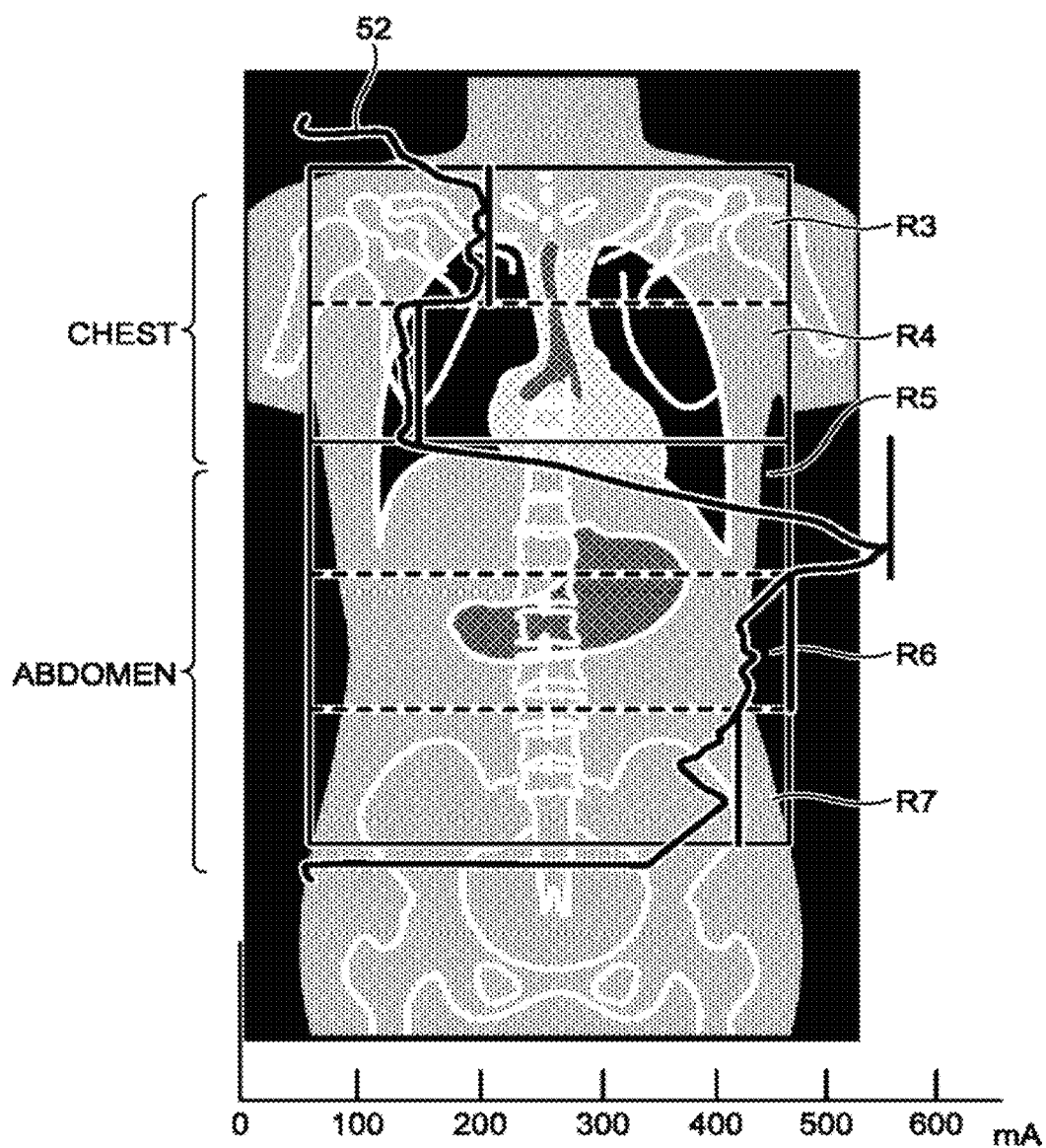
FIG. 8 is a diagram for explaining an example of processing with a setting function 37c according to the first embodiment.

The following is explanation of an example of processing with the setting function 37c according to the first embodiment, with reference to FIG. 7 and FIG. 8. FIG. 7 and FIG. 8 illustrate the case where the unit of calculating the tube current value is one rotation of the X-ray tube 12a, as an example. Specifically, FIG. 7 and FIG. 8 illustrate the case where the tube current value is calculated by AEC for each rotation of the X-ray tube 12a. FIG. 7 is a diagram for explaining an example of the case of calculating the tube current for each rotation of the X-ray tube 12a. FIG. 8 is a diagram for explaining an example of processing with the setting function 37c according to the first embodiment. FIG. 7 and FIG. 6 illustrate the scan range and a modulation curve of the tube current on the scanogram, and the divisions of a scale of the tube current value under the scanogram.

The following is explanation of the case where the tube current value is calculated for each rotation of the X-ray tube 12a, with reference to FIG. 7. FIG. 7 illustrates the case where the scanogram is acquired, and the chest and the abdomen are selected as the scan target regions. Specifically, the detecting function 37a detects regions from landmarks for the acquired scanogram as the target, and the setting function 37c sets the scan range to include the chest and the abdomen from the positions of the detected regions. The setting function 37c acquires information on the chest and the abdomen serving as the scan target regions, for example, from a scan protocol.

For example, as illustrated in FIG. 7, the setting function 37c sets the scan range including the chest and the abdomen. Each of area R3 to area R7 indicates an area scanned while the X-ray tube 12a makes one rotation. In other words, each of the area R3 to the area R7 indicates an area scanned with one rotation of the X-ray tube 12a. When AEC is executed with the scan range set as described above, the tube current value is set as illustrated with vertical lines in the respective areas of FIG. 7, and the tube current is modulated as illustrated with a curve 51. Specifically, in each of the area R3 to the area R7, absorption of X-rays is measured from the scanogram, and the tube current value of each area is calculated on the basis of the measured absorption. The calculated tube current value is set as the scan condition.

For example, as illustrated in FIG. 7, "200 mA" is set as the tube current value of the area R3, "250 mA" is set as the tube current value of the area R4, "550 mA" is set as the tube current value of the area R5, "450 mA" is set as the tube current value of the area R6, and "400 mA" is set as the tube current value of the area R7. When the tube current value is set as described above, the X-ray irradiation control circuitry 11 executes modulation control illustrated with the curve 51 of FIG. 7 to modulate the tube current value to the tube current value set in each area.

In this state, in the case where AEC is executed with the scan range simply set as illustrated in FIG. 7, when the calculation unit for which the tube current value is calculated includes a region with small X-ray absorption and a region with large X-ray absorption, dose of the region with small X-ray absorption may increase. For example, as illustrated in the area R4 of FIG. 7, when the area serving as the unit to calculate the tube current value includes the "liver" with large X-ray absorption and "lung field" with small X-ray absorption, in AEC, high tube current value is calculated and set, to secure the image quality of the "liver" with large X-ray absorption. As a result, X-ray is also applied to the "lung field", the image quality of which can be secured with low tube current value, with high tube current value.

For this reason, the setting function 37c according to the first embodiment specifies the boundary between the regions detected with the detecting function 37a, to adjust the calculation unit of the tube current value in accordance with the specified boundary. Specifically, the setting function 37c adjusts the scan range such that the calculation unit of the tube current value is partitioned in the boundary between the regions. As an example, when the scan range is set, the setting function 37c adjusts the scan range such that the area R4 does not include the liver, as illustrated in FIG. 6. Specifically, as illustrated in FIG. 8, the setting function 37c adjusts the scan range such that the boundary between the "lung field" and the "liver" in the axis direction agrees with the boundary between the area R4 and the area R5. For example, the setting function 37c adjusts the scan start position such that the position of the boundary agrees with the rotation period end portion coordinate of the tube bulb position in the area of scan used for mA calculation) of the X-ray tube. As an example, the setting function 37c sets the scan range to move the scan start position forward, to move the area scanned while the X-ray tube 12a makes one rotation toward the head side. In this manner, as illustrated in FIG. 8, the boundary between the "lung field" and the "liver" in the Z axis direction agrees with the boundary between the area R4 and the area R5.

In this state, when the scan range is adjusted, the setting function 37c adjusts the scan range such that the set scan target region is included in the scan range. For example, when the scan range is adjusted by moving the scan start position forward as illustrated in FIG. 8, in the case where the scan target region is included in a part up to the area R7, the setting function 37c sets the scan range without increasing the scanned areas. By contrast, when the scan target region comes out of the area R7 by moving the scan start position forward, the setting function 37c sets the scan range to cause the X-ray tube 12a to make one more rotation.

As described above, modulation of the tube current suitable for the region to be imaged is enabled by adjusting the scan range such that the calculation unit of the tube current value is partitioned in the boundary between the regions. For example, as illustrated in FIG. 8, the "liver" is excluded from the area R4, the tube current value is calculated on the basis of the X-ray absorption of the "lung field", and unnecessary radiation exposure of the "lung field" is reduced. As an example, as illustrated in FIG. 8, "150 mA" is set as the tube current value of the area R4. This results in reduction of the tube current value by "100 mA" in comparison with the value "250 mA" illustrated in FIG. 7, and enables reduction in dose of the "lung field".

In addition, with adjustment with the setting function 37c, the area R5 includes the whole "liver", as illustrated in SIG 8. This structure enables scan of the whole "liver" with large X-ray absorption with the same tube current value "550 mA", and reduces unevenness of the image quality of the "liver". Specifically, when scan is executed while modulation of the tube current is performed in the scan range as illustrated in FIG. 7, the portion of the "liver" included in the area R4 is scanned with "250 mA", and the portion of the "liver" included in the area R5 is scanned with "550 mA". Consequently, an image with different image qualities is generated in the same organ "liver". The X-ray CT apparatus 1 according to the first embodiment reduces such unevenness of image quality.

The setting function 37c is also capable of adjusting the scan range such that the scan target region is included in a calculation unit of the tube current value. For example, the setting function 37c is capable of adjusting the scan range such that the whole "liver" is included in the area scanned while the X-ray tube 12a makes one rotation. This structure enables scan of each of regions having different X-ray absorptions with a single tube current value, and enables modulation of the tube current suitable for the region to be imaged.

The embodiment described above illustrates the case adjusting the scan range, as adjustment of the setting range to set the tube current value in accordance with the boundary between the regions. However, the embodiment is not limited thereto, but the setting function 37c is capable of performing other various adjustments. The following is explanation of other adjustments performed with the setting function 37c.

For example, setting function 37c controls the rotary frame 15, the bed device 20, the gantry 10, and the detector 13 such that the boundary between the regions detected with the detecting function 37a agrees with the rotation period end portion (Z coordinate of the bulb tube position in the scan area used for calculation of mA) of the X-ray tube 12a. Specifically, the setting function 37c controls the rotation speed of the rotary frame 15, the send-out speed of the top board 22 in the bed device 20, the moving speed of the gantry 10, and the acquisition lines of the detector 13 such that the boundary between regions agrees with the rotation period end portion of the X-ray tube 12a in the Z axis direction. As an example, the setting function 37c controls the rotary frame 15, the bed device 20, the gantry 10, and the detector 13 such that the boundary between the "lung field" and the "liver" in the Z axis direction agrees with the partition between the calculation units of the tube current value.

The setting function 37c performs control in accordance with the imaging method. For example, when projection data is acquired by helical scan, the setting function 37c controls the rotary frame 15 rotating and moving the X-ray tube 12a, the relative positional relation between the top board 22 on which the subject lies down and the gantry 10, or the acquisition lines of the detector 13 such that the position of the boundary between the regions agrees with the rotation period end portion of the X-ray tube 12a. Specifically, in the case of performing acquisition by helical scan, while the top board 22 on which the subject lies down is sent out (or while the gantry 10 is moving), the rotary frame 15 rotates the X-ray tube 12a to acquire projection data. The setting function 37c controls the rotation speed of the rotary frame 15, the send-out speed (or moving speed of the gantry 10) of the top board 22, and the acquisition lines of the detector 13 such that the boundary between the regions agrees with the rotation period end portion (partition between the calculation units of the tube current value) of the X-ray tube 12a in the Z axis direction.

In addition, for example, when projection data is detected by wide volume scan (step-and-shoot), the setting function 37c controls the acquisition lines of the detector 13 such that the position of the boundary agrees with the rotation period end portion of the X-ray tube. Specifically, in the case of performing acquisition by wide volume scan, conventional scan is performed in a plurality of scan areas while the position of the top board 22 is moved at regular intervals, to acquire projection data. For this reason, the setting function 37c controls the acquisition lines of the detector 13 such that the Z axis end portion of the area that is scanned by one rotation of the X-ray tube 12a agrees with the boundary between the regions.

The embodiment described above illustrates the case where the tube current value is calculated for each rotation of the X-ray tube 12a, as an example. However, the embodiment is not limited thereto, but the calculation unit of the tube current value may be adjusted. Specifically, the setting function 37c may adjust the position of calculating the tube current value controlled by AEC in scan. As an example, the setting function 37c performs adjustment such that the tube current value is calculated for each view to acquire projection data. In this manner, for example, the tube current value based on X-ray absorption is calculated and set for each view for which scanogram is acquired. This structure enables modulation of the tube current to a tube current value suitable for the region included in each view.

As described above, the setting function 37c adjusts the scan range or the like such that the boundary between the regions in the Z axis direction agrees with the rotation period end portion (partition between the calculation units of the tube current value) of the X-ray tube 12a. The X-ray CT apparatus 1 according to the first embodiment is also capable of modulating the tube current in the X-Y direction, as well as modulation of the tube current in the Z axis direction. For example, the X-ray CT apparatus 1 sets the tube current value in the X direction and the Y direction for each rotation, and modulates the tube current to the set tube current value.

Figure 9:
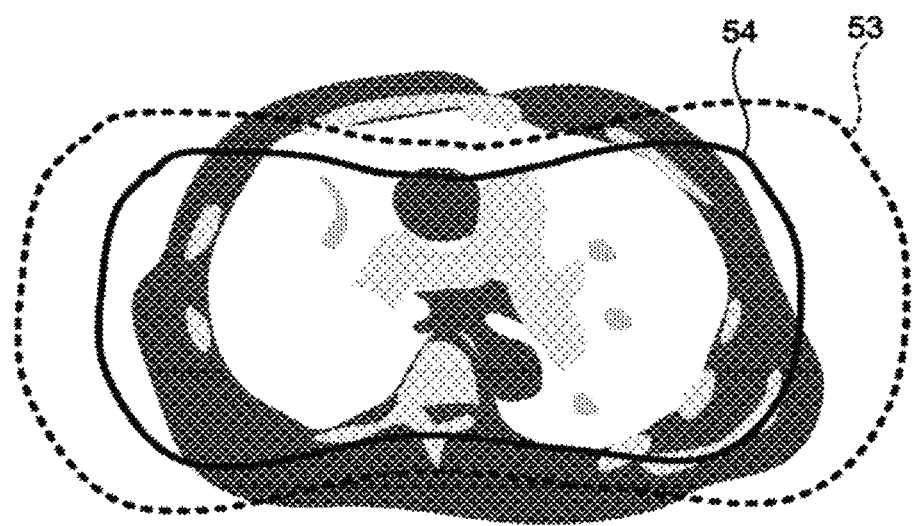
FIG. 9 is a diagram for explaining an example of modulation of the tube current in an X-Y plane according the first embodiment.

FIG. 9 is a diagram for explaining an example of modulation of the tube current in the X-Y plane according to the first embodiment. FIG. 9 illustrates a modulation curve of the tube current in an axial cross section of the area R4 in FIG. 8. A curve 54 is a modulation curve, and a distance of the curve 54 from the center illustrates intensity of the tube current. Specifically, the tube current becomes maximum in the Y axis direction (lateral direction), and the tube current becomes minimum in the "anterior posterior (AP) direction". For example, the setting function 37c sets the tube current value in the X axis direction and the Y axis direction, on the basis of the tube current value set in the area R4. Specifically, the setting function 37c sets the total tube current value during one rotation of the X-ray tube to "150 mA" set in the area R4 of FIG. 8. Thereafter, the setting function 37c distributes "150 mA" on the basis of the ratio of X-ray absorption in the X axis direction to X-ray absorption in the Y axis direction. In this manner, the setting function 37c executes modulation of the tube current illustrated with the curve 54 in FIG. 9.

A curve 53 illustrated in FIG. 10 illustrates a modulation curve in the case where the tube current value set for the area R4 is "250 mA". As illustrated in FIG. 10, the curve 54 has a shorter distance from the center than that of the curve 53. Specifically, X-rays applied to the "lung field" is reduced, by modulating the tube current value set for the area R4 to "150 mA".

As described above, the X-ray CT apparatus 1 according to the first embodiment is capable of modulating the tube current suitable for the region to be imaged, by causing the boundary between the regions to agree with the partition between the calculation units (for example, one rotation of the X-ray tube 12a). The X-ray CT apparatus 1 may include a mode to set the boundary between the regions. Specifically, the X-ray CT apparatus 1 includes "image quality priority mode" and "dose reduction mode", and sets the boundary between the regions in accordance with the modes.

For example, the setting function 37c sets one of the "dose reduction mode" and the "image quality priority mode", on the basis of a designation operation performed by the operator. For example, when the "image quality priority mode" is set and the first region and the second region overlap in the XY cross section, the setting function 37c sets the end portion of the region with a higher CT value in the first region and the second region, as the boundary. Specifically, in the "image quality priority mode", when a plurality of regions are included in the calculation unit (for example, one rotation of the X-ray tube 12a) of the tube current, the setting function 37c sets the end portion of the region with a higher CT value as the boundary, and adjusts the scan range or the like to cause the set boundary to agree with the partition between the calculation units of the tube current.

Figure 10A:
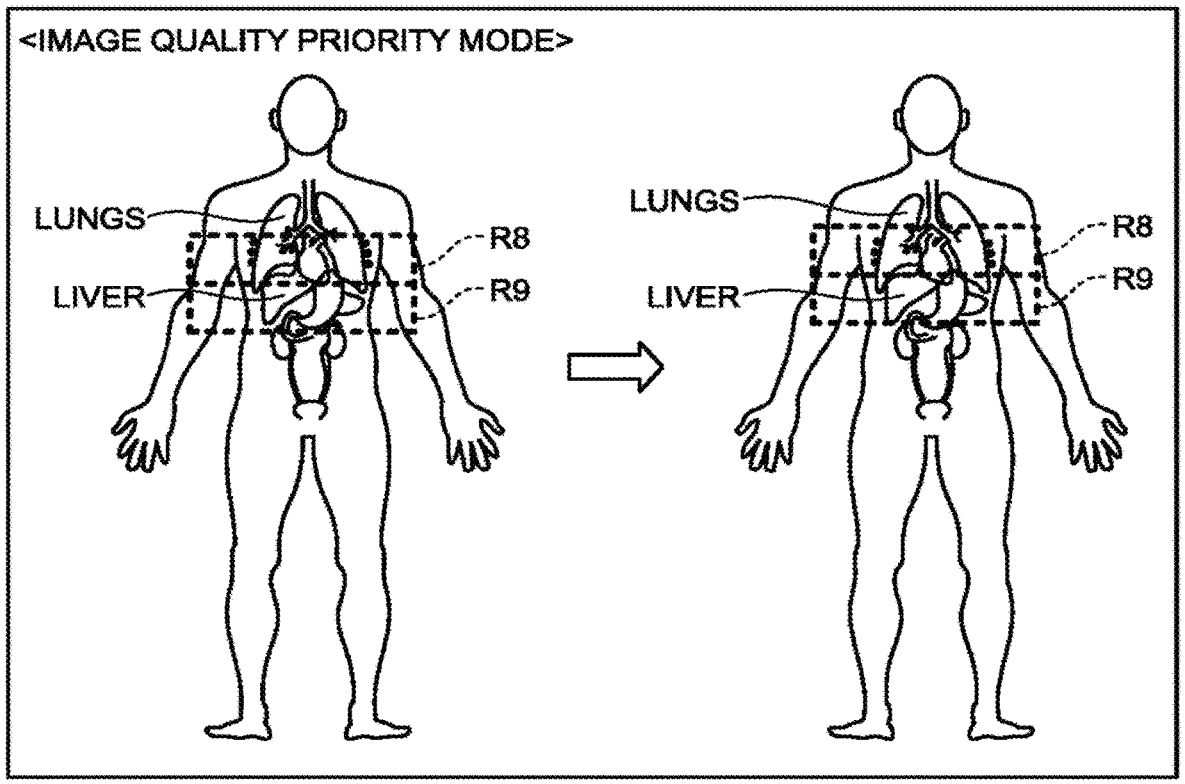
FIG. 10A is a diagram for explaining an example of processing in an "image quality priority mode" according to the first embodiment.

FIG. 10A is a diagram for explaining an example of processing in the "image quality priority mode" according to the first embodiment. FIG. 10A illustrates an example of processing in the "image quality priority mode" in the case where the "lung field" and the "liver" are included in the area R8 scanned while the X-ray tube 12a makes one rotation. For example, as illustrated in the left drawing of FIG. 10A, when the area R8 includes the "lung field" and the "liver" in the "image quality priority mode", the setting function 37c sets the end portion of the "liver" with a high CT value in the Z axis direction as the boundary between the "lung field" and the "liver", as illustrated in the right drawing of FIG. 10A. Thereafter, the setting function 37c adjusts the scan range or the like to cause the set boundary to agree with the boundary between the area R8 and the area R9.

By contrast, for example, when the "dose reduction mode" is set and the first region and the second region overlap in the XY cross section, the setting function 37c sets the end portion of the region with a lower CT value in the first region and the second region as the boundary. Specifically, in the "dose reduction mode", when a plurality of regions are included in the calculation unit (for example, one rotation of the X-ray tube 12a), the setting function 37c sets the end portion of the region with a lower CT value as the boundary, and adjusts the scan range or the like to cause the set boundary to agree with the partition between the calculation units of the tube current.

Figure 10B:
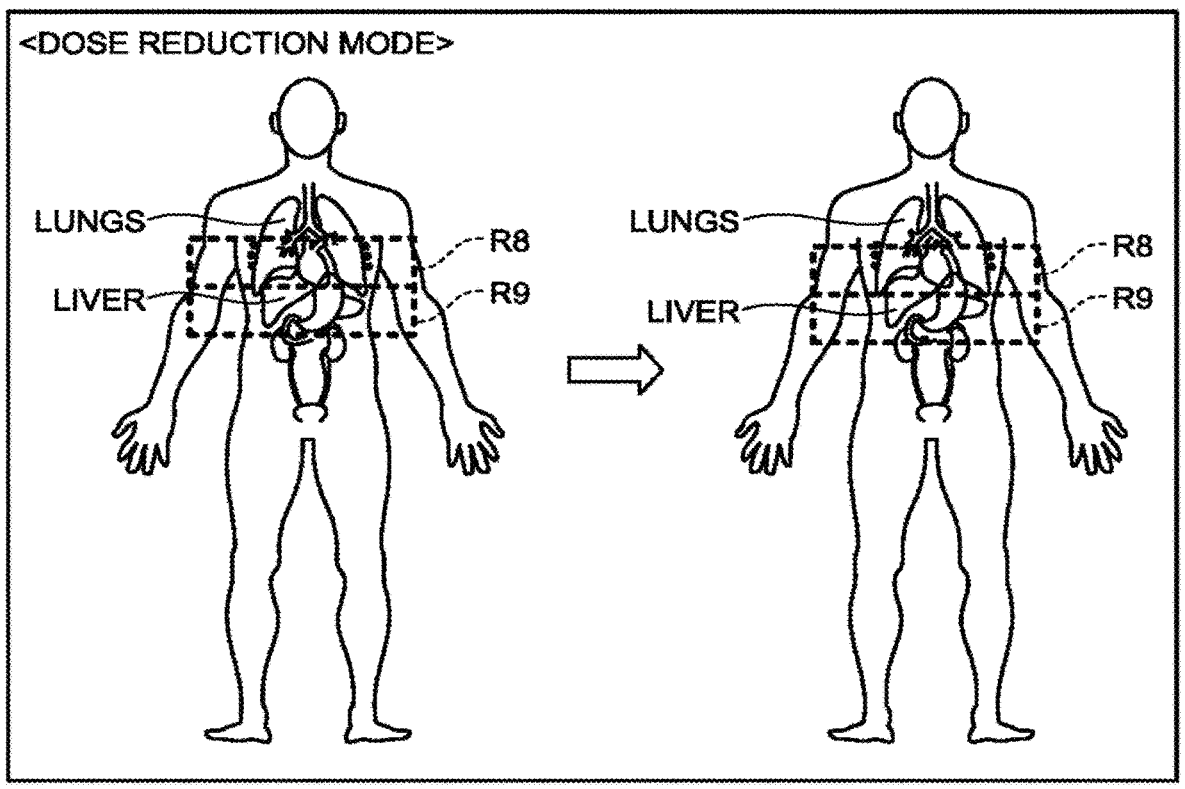
FIG. 10B is a diagram for explaining an example of processing in a "dose reduction mode" according to the first embodiment.

FIG. 10B is a diagram for explaining an example of processing in the "dose reduction mode" according to the first embodiment. FIG. 10B illustrates an example of processing in the "dose reduction mode" in the case where the "lung field" and the "liver" are included in the area R8 scanned while the X-ray tube 12a makes one rotation. For example, as illustrated in the left drawing in FIG. 10B, when the "lung field" and the "liver" are included in the area R8 in the "dose reduction mode", the setting function 37c sets the end portion of the "lung field" with a lower CT value in the Z axis direction as the boundary between the "lung field" and the "liver", as illustrated in the right drawing in FIG. 10B. Thereafter, the setting function 37c adjusts the scan range or the like to cause the set boundary to agree with the boundary between the area R8 and the area R9.

FIG. 10A and FIG. 10B illustrate the case where two regions ("lung field" and "liver") are included in the same area, but the embodiment is not limited thereto. The processing described above can be performed in other various regions. In addition, the number of regions is not limited to two, but processing can be performed in the same manner also for the case where three or more regions are included. In such a case, in the "image quality priority mode", an end portion of the region with the highest CT value among the three or more regions is set as the boundary. In the "dose reduction mode", an end portion of the region with the lowest CT value among the three or more regions is set as the boundary. The operator sets one of the "image quality priority mode" and the "dose reduction mode" as desired.

With reference to FIG. 2 again, the display control function 37d displays information adjusted with the setting function 37c on the display 32. For example, the display control function 37d displays information on the adjusted scan range, control information on the rotary frame 15, control information on the top board 22, control information on the gantry 10, and control information on acquisition lines of the detector 13, on the display 32. This structure enables the operator to check a result of adjustment with the setting function 37c. The X-ray CT apparatus 1 receives an execution operation (such as pressing of the exposure button) from the operator, to execute scan with the adjusted settings.

Figure 11:
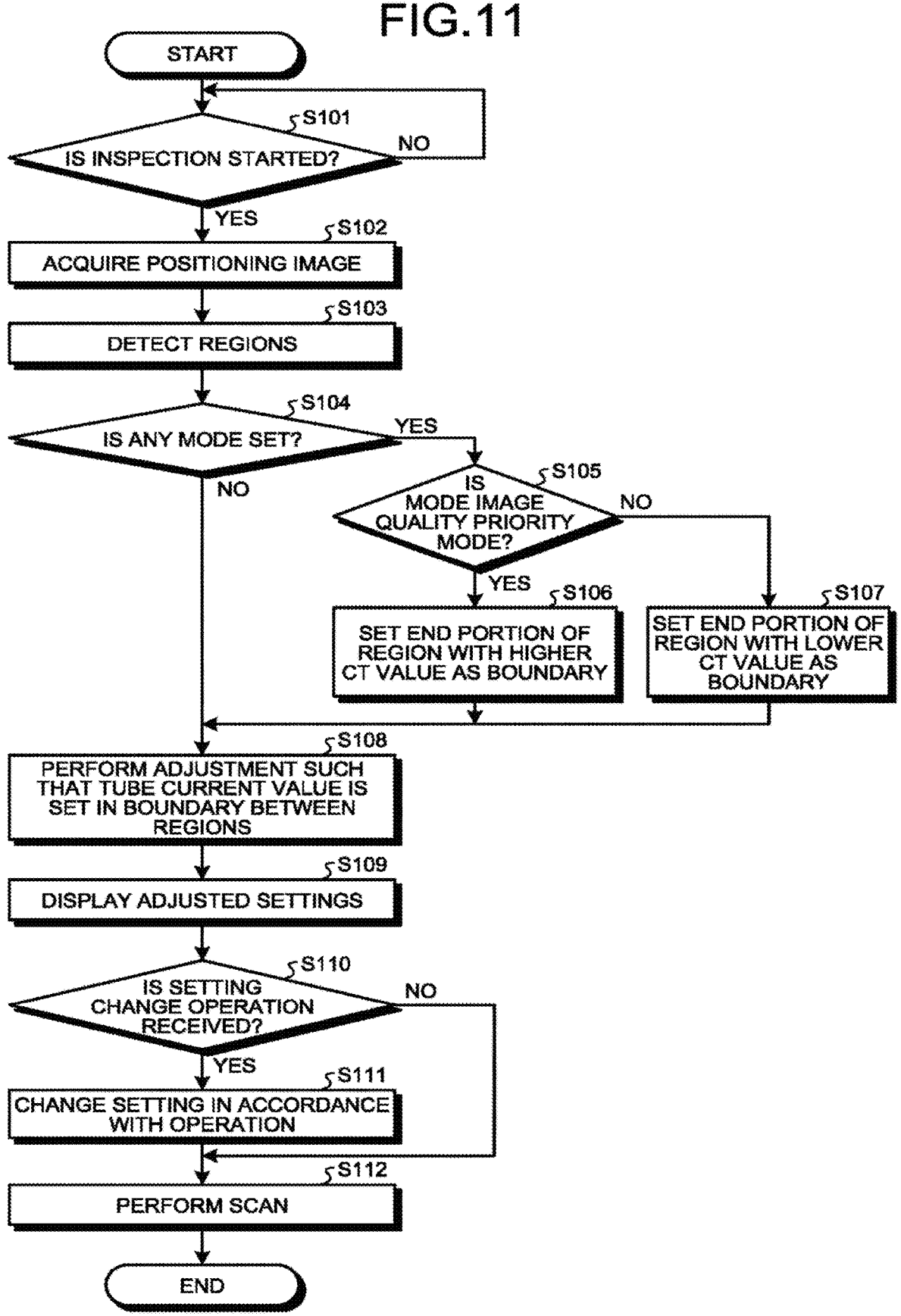
FIG. 11 is a flowchart illustrating a process of processing performed with the X-ray CT apparatus according to the first embodiment.

The following is explanation of processing of the X-ray CT apparatus 1 according to the first embodiment, with reference to FIG. 11. FIG. 11 is a flowchart illustrating process of processing with the X-ray CT apparatus 1 according to the first embodiment. Step S101 and Step S102 illustrated in FIG. 11 are steps executed with the processing circuitry 37 by reading a program corresponding to the processing function from the storage 35. At Step S101, the processing circuitry 37 determines whether inspection is started. At Step S102, the processing circuitry 37 controls the scan control circuitry 33 and the image reconstruction circuitry 36 and the like, to acquire three-dimensional positioning images scanogram).

Step S101 in FIG. 11 is a step executed with the processing circuitry 37 by reading a program corresponding to the detecting function 37a from the storage 35. At Step S103, the processing circuitry 37 detects regions from the scanogram. Step S104 of FIG. 11 is a step executed with the processing circuitry 37 by reading a program corresponding to the processing function from the storage 35. At Step S104, the processing circuitry 37 determines whether any mode is set. When no mode is set (No at Step S104), the process proceeds to Step S108. By contrast, when any mode is set (Yes at Step S104), the process proceeds to Step S105.

Step S105 to Step S108 in FIG. 11 are steps executed with the processing circuitry 37 by reading a program corresponding to the setting function 37c from the storage 35. At Step S105, the processing circuitry 37 determines whether the set mode is the "image quality priority mode". When the set mode is the "image quality priority mode" (Yes at Step S105), the process proceeds to Step S106, and the processing circuitry 37 sets an end portion of a region with a higher CT value as the boundary. By contrast, when the set mode is not the "image quality priority mode" (No at Step S185), the process proceeds to Step S107, and the processing circuitry 37 sets an end portion of a region with lower CT value as the boundary. Thereafter, at Step S108, the processing circuitry 37 performs adjustment to set the tube current at the boundary between the regions.

Step S109 in FIG. 11 is a step executed with the processing circuitry 37 by reading a program corresponding to the display control function 37d from the storage 35. At Step S109, the processing circuitry 37 displays the adjusted settings. Step S110 in FIG. 11 is a step executed with the processing circuitry 37 by reading the program corresponding to the processing function from the storage 35. At Step S110, the processing circuitry 37 determines whether a setting change operation is received. When a setting change operation is received (Yes at Step S110), the process proceeds to Step S111. By contrast, when no setting change operation is received (No at Step S110), the process proceeds to Step S112.

Step S111 in FIG. 11 is a step executed with the processing circuitry 37 by reading the program corresponding to the setting function 37c from the storage 35. At Step S111, the processing circuitry 37 changes the setting in accordance with the received operation. Step S112 in FIG. 11 is a step executed with the processing circuitry 37 by reading the program corresponding to the processing function from the storage 35. At Step S112, the processing circuitry 37 performs scan.

As described above, according to the first embodiment, the data acquisition circuitry 14 detects X-rays transmitted through the subject with the detector 13, and acquires projection data on the basis of the detection result. The image reconstruction circuitry 36 generates image data from the projection data. The detecting function 37a acquires positional information on a plurality of regions in the image data. The setting function 37c specifies the boundary between the first region and the second region in the image data, on the basis of positional information, and adjust the setting range to set the tube current value in accordance with the boundary. Accordingly, the X-ray CT apparatus 1 according to the first embodiment enables setting of the tube current value in the boundary between the regions, and modulation of the tube current suitable for the region to be imaged.

In addition, according to the first embodiment, the setting function 37c adjusts the scan start position such that the position of the boundary agrees with the rotation period end portion of the X-ray tube. This structure enables easy setting of the tube current value in the boundary between the regions.

According to the first embodiment, when the detection result is detected by helical scan, the setting function 37c controls the rotary frame rotating and moving the X-ray tube 12a, a relative positional relation between the top board 22 on which the subject lies down and the gantry 10, or the acquisition lines of the detector 13 such that the position of the boundary agrees with the rotation period end portion of the X-ray tube. Accordingly, the X-ray CT apparatus 1 according to the first embodiment enables agreement of the boundary between the regions with the rotation period end portion by various methods, when acquisition is performed by helical scan.

According to the first embodiment, when the detection result is detected by wide volume scan, the setting function 37c controls the acquisition lines of the detector such that the position of the boundary agrees with the rotation period end portion of the X-ray tube. Accordingly, the X-ray CT apparatus 1 according to the first embodiment enables agreement of the boundary between the regions with the rotation period end portion, also when acquisition is performed by wide volume scan.

According to the first embodiment, the detecting function 37a acquires positional information relating to a plurality of regions in image data, by matching image data with anatomical reference positions. Accordingly, the X-ray CT apparatus 1 according to the first embodiment enables more accurate detection of regions.

In addition, according to the first embodiment, when the "dose reduction mode" is set and the first region and the second region overlap in the XY cross section, the setting function 37c sets an end portion of a region with a lower CT value in the first region d the second region as the boundary. Besides, when t "image quality priority mode" is set and the first region and the second region overlap in the XY cross section, the setting function 37c sets an end portion of a region with a higher CT value in the first region and the second region as the boundary. Accordingly, the X-ray CT apparatus 1 according to the first embodiment enables setting of the boundary in accordance with circumstances.

Second Embodiment

The first embodiment has been described above, but an embodiment may be carried out in various different forms other than the first embodiment described above.

The first embodiment described above illustrates the case where an end portion of a region with a lower CT value is set as the boundary in the "dose reduction mode", and an end portion of a region with a higher CT value is set as the boundary in the "image quality priority mode". However, the embodiment is not limited thereto, but, for example, tissue weighting factors of the regions may be taken into consideration. In such a case, for example, when the "dose reduction mode" is set, the setting function 37c sets the boundary between the regions, on the basis of tissue weighting factors of respective regions included in the calculation unit of the tube current value. For example, the calculating function 37b sets an end portion of a region with the highest tissue weighting factor among the regions included in the calculation unit of the tube current value. The setting function 37c performs control such that the tube current value is set on the basis of the tissue weighting factor of the region including the end portion set as the boundary. The calculating function 37b may calculate the dose information for the region including the end portion set as the boundary, and the setting function 37c may perform control to set the tube current value on the basis of the calculated dose information.

For example, the calculating function 37b calculates dose information for each region using "dose length product (DLP)". The "DLP (mGy·cm)" is a value obtained by multiplying the absorbed dose "$CTDI_{Vol}$ (mGy)" measured with a CT dose index (CTDI) phantom by the X-ray irradiation range in the body axis direction. The absorbed doses "$CTDI_{Vol}$ (mGy)" are measured in advance under respective various conditions with a head CTDI phantom with a diameter of "160 mm" and an abdomen CTDI phantom with a diameter of "320 mm", and stored in the X-ray CT apparatus 1. Specifically, DLP is calculated from the "$CTDI_{Vol}$ (mGy)" and the X-ray irradiation range corresponding to each X-ray irradiation condition. The calculating function 37b calculates dose information for each region, by multiplying the "DLP" calculated in accordance with the X-ray irradiation conditions of scan by the factor for each "tissue/organ".

The example described above illustrates the case of setting the boundary between the regions in accordance with the tissue weighting factor. However, the embodiment is not limited thereto, but, for example, the scan range and/or the rotation orbital path of the X-ray tube 12a may be adjusted in accordance with the tissue weighting factor. In such a case, the setting function 37c adjusts the scan range and/or the rotation orbital path of the X-ray tube 12a in accordance with the tissue weighting factor of each region included in the scan range. As an example, the setting function 37c adjusts the scan range and the rotation orbital path of the X-ray tube 12a such that application of direct radiation of X-rays to the region including the value of the tissue weighting factor exceeding a predetermined value is reduced, in regions included in the scan range.

Specifically, the setting function 37c adjusts the scan range and the rotation orbital path of the X-ray tube 12a such that application of X-rays to the region with high tissue weighting factor value is reduced, on the basis of a three-dimensional positional relation between the regions detected with the detecting function 37a and the X-ray tube 12a rotated with the rotary frame 15. For example, the etting function 37c adjusts the scan range and the rotation orbital path of the X-ray tube 12a such that X-rays are applied to the region with high tissue weighting factor value from back side (side with the longer distance from the body surface). This structure further reduces the dose of the subject.

The first embodiment described above illustrates the case of acquiring the scanogram in a three-dimensional manner, but the embodiment is not limited thereto. The scanogram may be acquired in a two-dimensional manner. In such a case, the detecting function 37a detects regions from two-dimensional scanogram.

The first embodiment described above illustrates the case of setting the tube current value to correspond to the region with large X-ray absorption (for example, region with the maximum X-ray absorption), to secure the image quality of the region with large X-ray absorption in the calculation unit for which the tube current value is calculated. However, the embodiment is not limited thereto, but the setting of the tube current value can properly be changed. For example, the setting function 37c calculates an average value of X-ray absorptions in the calculation unit for which the tube current value is calculated. The setting function 37c can set a tube current value corresponding to the calculated average value as the tube current value in the calculation unit.

The first embodiment described above illustrates the case of using one rotation of the X-ray tube 12a, or a view to acquire projection data, as the calculation unit for which the tube current value is calculated. However, the embodiment is not limited thereto, but a calculation unit may be used properly. For example, there are cases where the unit for which a tube current value can be set differs between X-ray CT apparatuses. Specifically, X-ray CT apparatuses may have different control units (calculation units) for modulation of the tube current value, and may be capable of setting the tube current value in various units. Accordingly, the calculation unit for which the tube current value is calculated may properly be set according to various circumstances, for example, for each apparatus, for each inspection order, or for each subject.

In other words, the setting function 37c is capable of adjusting setting of scan conditions, on the basis of the boundary and the control unit for the tube current value. Specifically, the setting function 37c adjusts the scan start position such that the position of the boundary agrees with the end portion of the imaging range corresponding to the control unit equal to or larger than the minimum control unit for the tube current value, in the slice direction. For example, when "90° rotation" of the X-ray tube 12a can be set as the minimum control unit (minimum calculation unit) for the tube current value, the setting function 37c adjusts the scan range such that the boundary between the regions agrees with the end portion of the calculation unit with the calculation unit of "90° rotation" or more of the X-ray tube 12a.

As an example, the setting function 37c adjusts the scan range (adjusts the scan start position) such that the boundary (such as the boundary between the "lung field" and the "liver") between the regions in the Z axis direction agrees with the end portion of "90° rotation" of the X-ray tube 12a. The etting function 37c is also capable of controlling the rotation speed of the rotary frame 15, the send-out speed of the top board 22 in the bed device 20, the moving speed of the gantry 10, and the acquisition lines of the detector 13 such that the boundary between the regions in the Z axis direction agrees with the end portion of "90° rotation" of the X-ray tube 12a.

The setting function 37c is capable of determining the end portion of the calculation unit to agree with the boundary between the regions, in consideration of the total tube current value of tube current values of the respective calculation units. As described above, the setting function 37c is capable of performing control such that the end portion of the calculation unit equal to or larger than the minimum control unit (minimum calculation unit) of the tube current value agrees with the boundary between the regions. Specifically, the X-ray CT apparatus 1 is capable of controlling the tube current value with fine control units, and performing control such that the boundary at which X-ray absorption markedly changes agrees with the end portion of the calculation unit.

The setting function 37c is capable of selecting the end portion of the calculation unit to be caused to agree with the boundary of the region such that the total of the tube current values of the respective control units becomes minimum. For example, in the case of causing the boundary of the regions to agree with the end portion of the calculation unit by adjusting the scan start position in the Z axis direction, the setting function 37c calculates each of total values of the tube current values in the case where the end portion of each calculation unit is caused to agree with the boundary between the regions. Thereafter, the setting function 37c selects a pair of the boundary and the end portion with the minimum total value, among the calculated total values. In addition, the setting function 37c adjusts the scan range such that the boundary and the end portion of the selected pair agree with each other. Even when the scan range includes a plurality of boundaries at which X-ray absorption markedly changes, the setting function 37c is capable of adjusting the scan range such that the total of tube current values of the respective control units becomes minimum, in the same manner as the processing described above.

The setting function 37c is also capable of properly changing the calculation unit for which the tube current value is calculated, in accordance with the total tube current value in the scan range. For example, the setting function 37c compares the total tube current value in the case where the end portion of "90° rotation" of the X-ray tube 12a is caused to agree with the boundary between the regions with the total tube current value in the case where the end portion of "180° rotation" of the X-ray tube 12a is caused to agree with the boundary between the regions. When the total tube current value of "180° rotation" is lower, the setting function 37c sets the calculation unit for which the tube current value is calculated to "180° rotation", and sets the scan conditions such that the end portion of the set calculation unit agrees with the boundary between the regions.

As described above, the setting function 37c is capable of setting the scan conditions such that the end portion in the control unit equal to or larger than the minimum control unit of the tube current value agrees with the boundary between the regions. The minimum control unit in control of the setting function 37c is each view, as described above. In such a case, for example, when X-rays are detected with a multi-line detector, the setting function 37c specifies the boundary between acquisition lines agreeing with the boundary between the regions, and controls the detector 13 detect X-rays with the specified acquisition line as the boundary.

As described above, the X-ray CT apparatus 1 is capable of modulating the tube current suitable for the region to be imaged, by performing control to cause the boundary between regions with different X-ray absorptions to agree with the boundary of the control unit of the tube current value, and capable of reducing the dose. For example, the X-ray CT apparatus 1 enables scan with tube current values suitable for the respective regions, even when the scan range includes regions with markedly different X-ray absorptions, under the condition in which image standard deviation (SD) is fixedly set.

For example, when image SD is set for each region and the present embodiment is not applied, dose may further increase, according to the set image SD. For example, in the case where the image SD for the "liver" is set lower, and the image SD of the "lung field" is set higher, when the "liver" and the "lung field" are included in the calculation unit of the tube current value, higher tube current value is set on the basis of the image SD set for the "liver", and dose for the "lung field" further increases. By contrast, when the present embodiment is applied, because the boundary between the "liver" and the "lung field" is caused to agree with the end portion of the calculation unit of the tube current value, an image can be acquired with image SDs set for the respective regions, without increasing the dose.

Each of constituent elements of the devices illustrated in the first embodiments is a functional and conceptual one, and is not always required to be physically configured as illustrated. Specifically, specific forms of distribution and integration of the devices are not limited to those illustrated, but the whole or part of them may be distributed or integrated functionally or physically in desired units, in accordance with various loads and/or use circumstances. In addition, the whole or any part of each of processing functions executed in each of the devices may be achieved with a CPU and a program analyzed and executed in the CPU, or achieved as hardware by wired logic.

The control method explained in the first embodiment may be achieved by executing a prepared control program with a computer, such as a personal computer and a workstation. The control program can be distributed through a network, such as the Internet. The control program may be stored in a computer-readable recording medium, such as a hard disk, a flexible disc (FD), a CD-ROM, an MO, and a DVD, and executed by being read out of the recording medium with the computer.

As explained above, each embodiment enables modulation of the tube current suitable for the region to be imaged.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography (CT) apparatus comprising:
   processing circuitry configured to
   generate image data based on a detection result obtained by detecting X-rays transmitted through a subject with a detector; and
   specify a boundary between a first region and a second region in the image data, based on anatomical landmarks in the image data, and adjust setting of scan conditions relating to a tube current value in accordance with a position of the boundary and a position of an end portion of a satiric range where the tube current value is set by Auto Exposure Control (AEC).

2. The X-ray CT apparatus according to claim 1, wherein the processing circuitry is configured to adjust a scan start position such that the position of the boundary agrees with an end portion of an imaging range corresponding to the setting range equal to or larger than a minimum setting range, in a slice direction.

3. The X-ray CT apparatus according to claim 2, wherein the processing circuitry is configured to set, based on a plurality of pieces of body thickness information on the subject in an imaging range determined by setting of the scan start position, the tube current value in the imaging range.

4. The X-ray CT apparatus according to claim 3, wherein the processing circuitry is configured to set the tube current value in the imaging range, based on a maximum body thickness or an average body thickness of the pieces of body thickness information on the subject in the imaging range.

5. The X-ray CT apparatus according to claim 1, wherein the processing circuitry is configured to adjust a scan start position such that the position of the boundary agrees with an end portion of an imaging range corresponding to a rotation period of an X-ray tube, in a slice direction.

6. The X-ray CT apparatus according to claim 1, wherein, when the detection result is detected by helical scan, the processing circuitry is configured to control a rotary frame rotating and moving an X-ray tube, a relative positional relation between a bed on which the subject lies down and a gantry, or acquisition lines of the detector such that the position of the boundary agrees with an end portion of an imaging range corresponding to a rotation period of the X-ray tube.

7. The X-ray CT apparatus according to claim 1, wherein, when the detection result is detected by wide volume scan, the processing circuitry is configured to control acquisition lines of the detector such that the position of the boundary agrees with an end portion of an imaging range corresponding to a rotation period of the X-ray tube.

8. The X-ray CT apparatus according to claim 1, wherein the processing circuitry is configured to acquire the anatomical landmarks in the image data by matching the image data with anatomical reference positions.

9. The X-ray CT apparatus according to claim 1, wherein the processing circuitry is configured to adjust a position of an imaging range for the first region and the second region, based on respective tissue weighting factors of the first region and the second region.

10. The X-ray CT apparatus according to claim 1, wherein the processing circuitry is further configured to set one of a dose reduction mode and an image quality priority mode, wherein
the processing circuitry is configured to set an end portion of a region with a lower CT value in the first region and the second region as the boundary, when the dose reduction mode is set and the first region and the second region overlap in an XY cross section.

11. The X-ray CT apparatus according to claim 1, wherein the processing circuitry is further configured to set one of a dose reduction mode and an image quality priority mode, wherein
the processing circuitry is configured to set an end portion of a region with a higher CT value in the first region and the second region as the boundary, when the image quality priority mode is set and the first region and the second region overlap in an XY cross section.

* * * * *